United States Patent [19]

Neuwirth et al.

[11] Patent Number: 5,159,925
[45] Date of Patent: Nov. 3, 1992

[54] CAUTERIZING APPARATUS AND METHOD FOR LAPAROSCOPIC CHOLECYSTOSTOMY, GALLBLADDER ABLATION AND TREATMENT OF BENIGN PROSTATE HYPERTROPHY

[75] Inventors: Robert S. Neuwirth, Englewood, N.J.; Lee R. Bolduc, Raleigh, N.C.

[73] Assignee: Gynelab, Inc., Raleigh, N.C.

[21] Appl. No.: 646,669

[22] Filed: Jan. 28, 1991

Related U.S. Application Data

[60] Continuation-in-part of Ser. No. 565,154, Aug. 9, 1990, Pat. No. 5,105,808, which is a division of Ser. No. 242,730, Sep. 9, 1988, Pat. No. 4,949,718.

[51] Int. Cl.⁵ .............................................. A61F 7/12
[52] U.S. Cl. .................................... 128/401; 606/28
[58] Field of Search ............................. 128/399–402; 606/27, 28

[56] References Cited

U.S. PATENT DOCUMENTS

| | | | |
|---|---|---|---|
| 2,043,083 | 6/1936 | Wappler | 128/401 |
| 2,190,384 | 7/1937 | Newman | 128/401 |
| 4,160,455 | 7/1979 | Law | 128/401 |
| 4,638,806 | 1/1987 | Bartlett | 128/401 |
| 4,754,752 | 7/1988 | Ginsburg et al. | 606/27 |
| 4,799,479 | 1/1989 | Spears | 606/28 |

FOREIGN PATENT DOCUMENTS 895046  12/1953  Fed. Rep. of Germany ...... 128/401

Primary Examiner—Max Hindenburg
Attorney, Agent, or Firm—Kenyon & Kenyon

[57] ABSTRACT

A method for a laparoscopic cholecystostomy and prostate or gallbladder ablation is disclosed wherein a bladder catheter is inserted into the prostate or gallbladder then heated for a period sufficient to cause cauterization necrosis of the tissue lining of the prostate of gallbladder. Subsequently, the prostate or gallbladder is allowed to drain and is then removed. An apparatus for performing the procedure and a procedure and apparatus for treatment of benign prostate hypertrophy are also disclosed.

6 Claims, 6 Drawing Sheets

CAUTERIZING APPARATUS AND METHOD FOR LAPAROSCOPIC CHOLECYSTOSTOMY, GALLBLADDER ABLATION AND TREATMENT OF BENIGN PROSTATE HYPERTROPHY

BACKGROUND OF THE INVENTION

This is a continuation-in-part application of U.S. Pat. application Ser. No. 565,154, filed Aug. 9, 1990, now U.S. Pat. No. 5,105,808 which is a divisional application of U.S. application Ser. No. 242,730, filed Sept. 9, 1988 and now U.S. Pat. No. 4,949,718.

FIELD OF THE INVENTION

This invention relates to laparoscopic general surgery and, particularly to a cauterizing apparatus and method for performing laparoscopic cholecystostomies and prostate or gallbladder ablation. More specifically, the apparatus and method of the present invention ensures effective necrosis of the gallbladder's tissue lining without the disadvantages of known laser assisted and chemical ablation techniques. In addition, an apparatus and method for treatment of benign prostate hypertrophy (BPH) is disclosed which effectively cauterizes and destroys the surface mucosa and more superficial layers of the prostate gland at the urinary bladder neck with the disadvantages of resectoscopic removal of the prostate.

BACKGROUND OF THE INVENTION

The following terms as used herein have the meaning given below:

"Cholethiasis" is gallbladder disease due to stones.

The "mucosa" is the lining tissue of the gallbladder, prostate, and the urinary bladder.

"Necrosis" means the death of cells in tissue.

"Benign prostate hypertrophy (BPH)" is non-cancerous overgrowth of the prostate causing obstruction to urine outflow from the urinary bladder.

The standard treatment of cholelithiasis is surgical removal of the gallbladder. Until quite recently, the open surgical removal technique has been the treatment of choice, with over half a million procedures being performed annually. Standard cholecystostomies remove the offending organ, thereby decreasing the patient's chances of recurrent problems. This treatment has a number of significant disadvantages, however, including those associated with major surgery, lengthy hospitalization and several weeks absence from work; all of which may result in a major economic impact to the patient. Because of these serious drawbacks, improved techniques for the treatment of cholelithiasis have been long sought. This search has lead to a movement towards non-invasive methods for the management of gallbladder disease.

The treatment of cholelithiasis has more recently evolved to the use of a laparoscope. Some laparoscopic techniques for cholecystostomies involved the percutaneous chemical destruction of the gall bladder. For example, gallbladder ablation has been described by Becker et al. through a technique involving cystic duct occlusion combined with transcatheter chemical sclerotherapy, so as not to affect the bile ducts beyond the site of occlusion or otherwise cause other systemic or local side effects. In particular, Becker et al. describe cystic duct occlusion to prevent escape of sclerosant via the duct, followed by sclerotherapy of the tissue lining of the gallbladder with a sclerosant, e.g., ethanol or STS. This technique is cumbersome, however, inasmuch as it requires a separate step to achieve cystic duct occlusion and, at the same time, suffers from problems associated with introducing dangerous chemicals to a patient's body. Unfortunately, complications have been reported for these types of non-invasive procedures, including bile peritonitis and respiratory arrest which have occurred with the use of ether.

The use of a laparoscope as a diagnostic tool for pelvic and abdominal pain has enjoyed increased attention over the last few years as a result of advances in the use of fiber lasers and newer laparoscopic instrumentation.

The laparoscopic cholecystostomy has become a practical alternative to common surgical techniques because it reduces incisions and significantly decreases the amount of postoperative pain associated with the traditional techniques. Further advantages include short stay treatment and earlier resumption of normal activities; usually within as few as 7 days. Known laser laparoscopic cholecystostomy procedures are not without risk, however, and require a significant level of expertise and proficiency in the use of the fiber laser or electrosurgical equipment and all accessory instruments essential to prevent complications inherent to the laparoscope.

Accordingly, recently advanced methods for achieving laparoscopic cholecystostomies, including use of lasers, electrosurgery and chemical baths to effect necrosis of the affected tissue, while generally preferable to surgical removal of the gallbladder, suffer from disadvantages which have inhibited their widespread adoption.

The standard treatment of BPH is transurethral resection of the prostate. These procedures visualize the urinary bladder neck and the bulge of the hypertrophied prostate and remove part of the prostate by cutting and coagulative electrosurgery applied through the resectoscope. This treatment has significant disadvantages including exposure to electrosurgical burn, infusion of liquid distention media into the patient's vascular system that could cause congestive heart failure and serious electrolyte disturbances, hemorrhage from the prostate, and hospitalization.

Because of these problems, improved technology for treatment of BPH has been sought. Other approaches to this problem have been bladder dilation of the urinary bladder neck, cryocoagulation of the prostate, and drug therapies to shrink the prostate or improve urinary bladder function. None of these methods has effectively replaced the transurethral prostatectomy with the urologic resectoscope. In contrast, the apparatus and method of the present invention effectively cauterizes and destroys the surface mucosa and superficial layers of the prostate gland at the urinary bladder neck without the disadvantages of resectoscopic removal of the prostate.

ADVANTAGES AND SUMMARY OF THE INVENTION

It is an advantage of this invention to provide a method and apparatus for performing cholecystostomies which has the advantages associated with use of a laparoscope, but does not suffer from the disadvantages of known techniques which rely on laser, electrosurgical and chemical ablation.

Another advantage of the invention is to provide a method and apparatus for performing partial prostatectomies which avoids the risks of transurethral prostatectomy with the resectoscope while providing the advantages of the transurethral approach to prostate destruction.

The present invention provides a method for effecting necrosis of gallbladder mucosa or prostate which comprises the steps of inserting a distendable bladder into the gallbladder; inflating the distendable bladder with liquid; heating the liquid in the distendable bladder to a temperature and for a period of time effective for necrosing mucosa; deflating the distendable bladder; and removing it from the gallbladder or prostate.

The present invention also provides a method for effecting necrosis of the gallbladder's mucosa comprising the steps of making an incision into the abdominal cavity; inflating the abdomen with carbon dioxide so as to separate the abdominal wall from the organs within the abdomen; visualizing the gallbladder and liver with a laparoscope; grasping the gallbladder with a first puncture clamp; exposing the cystic duct with an electrosurgical hook; using a clip applicator to doubly clip the exposed cystic duct with first and second clips; grasping the gallbladder tip with a second puncture clamp so as to stabilize it; crushing stones in the stabilized gallbladder with a crushing forceps; puncturing the tip of the gallbladder with a 4 mm trocar and cannula; draining out the bile and crushed stones from the punctured gallbladder; irrigating the drained gallbladder with Ringer's Lactate so as to clean the mucosa; removing the irrigation catheter through the irrigation cannula; inserting a distendable bladder into the puncture site; inflating the inserted distendable bladder with a liquid to an appropriate volume in order to assure the distendable bladder's contact with substantially all of the gallbladder's tissue lining; heating the liquid to about 190° fahrenheit for a period of about 2 to 6 minutes so as to cauterize the tissue lining; monitoring the heating phase with the laparoscope; deflating the distendable bladder at the end of the heating phase; withdrawing the deflated distendable bladder from the gallbladder; inserting a 4 mm bladder catheter drain into the gallbladder puncture site left open where the distendable bladder was removed; inflating the inserted distendable bladder catheter drain in order to anchor it within the gallbladder; suturing the inflated distendable bladder catheter drain to the abdominal wall; removing the laparoscope, and the first and second puncturing clamps; and closing the wounds.

The present invention also provides an apparatus for effecting necrosis of the gallbladder tissue lining comprising a catheter adapted for insertion into the gallbladder, said catheter having a proximal end and a distal end, and a distendable bladder attached to said proximal end; inflating means connected to said distal end for inflating said distendable bladder; and control means for regulating the distending and heating of said distendable bladder.

The present invention also provides a method for effecting removal of urinary bladder neck blockage in a hypertrophied prostate by destroying it with heat causing coagulative necrosis of the prostate, preferably to a depth of about five to six millimeters without the need to perform a resectoscopic operation. This procedure involves insertion of a distendable bladder into the bladder after cystoscopy, filling the urinary bladder with sorbitol, revealing the nature of the interior of the urinary bladder and the configuration of the enlarged prostate, inflating the distendable bladder with about 10 ml. of sterile 5% dextrose in water; retracting the distendable bladder against the urinary bladder neck and the hypertrophied prostate, heating the fluid in the distendable bladder to about 195° Fahrenheit for about 5 minutes; deflating the distendable bladder and withdrawing it from the urinary bladder and urethra; then inserting an indwelling foley catheter for about seven days to provide urine outflow during the period of swelling and edema following the heat injury.

The present invention provides an apparatus for effecting necrosis of gallbladder tissue lining (mucosa), prostate and urinary bladder neck mucosa comprising a catheter adapted for insertion into the urinary bladder, said catheter having a proximal and distal end, and a distendable bladder attached to said proximal end; inflating means connected to said distal end for inflating said distendable bladder and control means for regulating the distending and heating of said distendable bladder.

DESCRIPTION OF THE PREFERRED EMBODIMENTS

Figure 1:
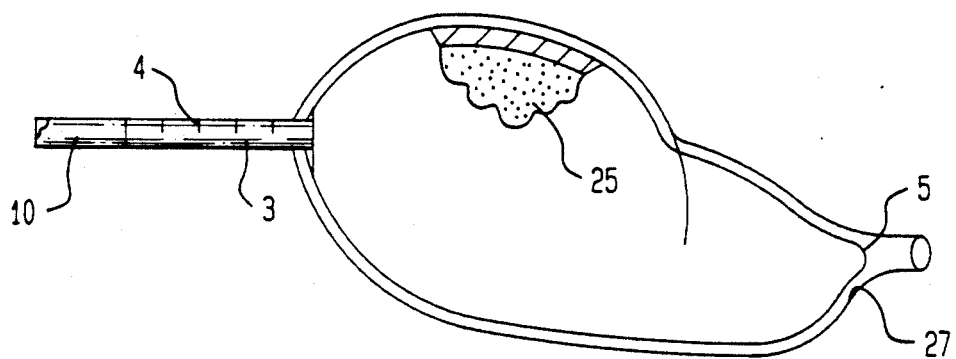
FIG. 1 illustrates a distendable bladder utilized in the method of the present invention which has been inserted into and inflated within a gallbladder.

FIG. 1 shows an inflated distendable bladder 5 attached to rigid tubing 3 located within a gallbladder 6. Inflation of the distendable bladder 5 with a fluid 25 assures uniform contact of the distendable bladder with the tissue lining (mucosa) 27 of the gallbladder 6.

The rigid tubing 3 and the attached distendable bladder 5 must be sufficiently small, when the distendable bladder is deflated, so that it can be conveniently and safely inserted into the gallbladder 6 through a punctured tip 22 of the gallbladder. The rigid tubing with the deflated distendable bladder is aligned with the gallbladder after the gallbladder is exposed with an electrosurgical hook (not shown) and grasped with a puncture clamp 4. After the distendable bladder 5 has been inserted, the distendable bladder 5 should be inflated to a pressure sufficient to ensure firm contact with the tissue to be necrosed, in this case the tissue on the interior gallbladder surface, but should preferably be maintained at or about 20 to 40 mmHg, and preferably about 30 mmHg, to minimize risk of rupture of the distendable bladder 5.

Distendable bladder 5 must be capable of withstanding high temperatures without rupturing, and preferably have as good a heat transfer characteristic as is obtainable in such materials to provide efficient heating action. A distendable bladder of a heat curing rubber such as latex has been found satisfactory.

Fluid 25 should be a sterile non-toxic fluid with a boiling point of about 212° F. A five percent dextrose in water solution has been found satisfactory.

Figure 2:
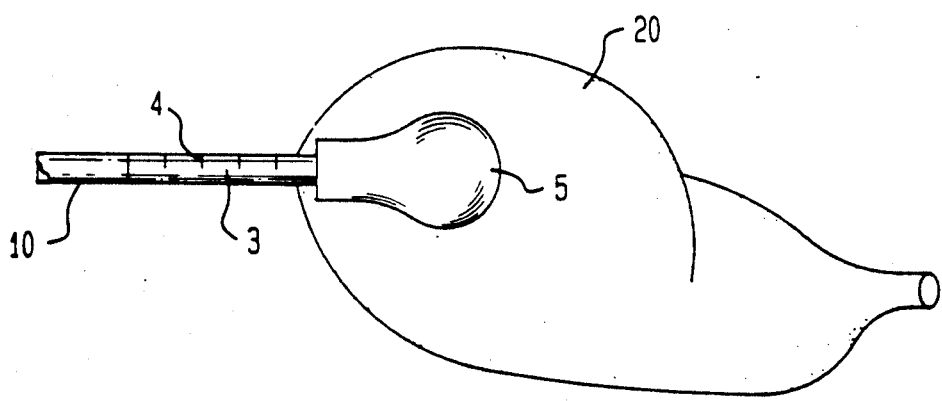
FIG. 2 illustrates placement of the distendable bladder within a gallbladder.

As illustrated in FIG. 2, the uninflated distendable bladder 5 attached to rigid tubing 3 is inserted into the abdominal cavity 21 for placement in the gallbladder 6. Placement may be aided by the scale gradations 4 located on the rigid tubing 3 to indicate the depth of insertion of the distendable bladder 5. Rigid tubing 3 is attached to a control unit 30 (shown in FIG. 5) via flexible tubing 10.

Figure 3:
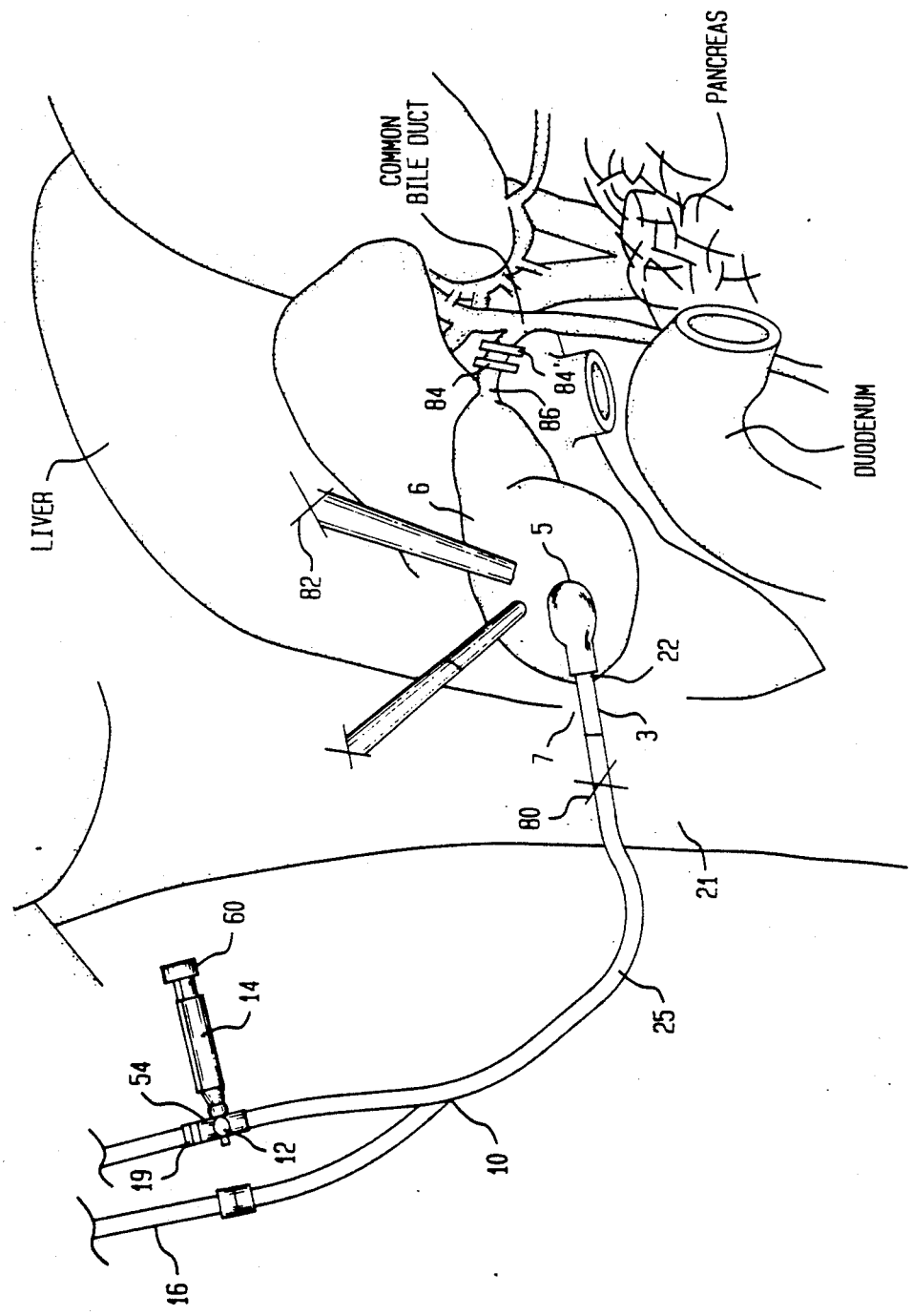
FIG. 3 is a cutaway view of the abdomen illustrating insertion the distendable bladder.

FIG. 3 is a cutaway view of the abdomen 21 illustrating insertion of the distendable bladder 5 into the gallbladder 6. For reference, the position of the gallbladder viz. the liver, pancreas and duodenum is illustrated. As can be seen, distendable bladder 5, which is attached to a proximal end 7 of rigid tubing 3 has been inserted into the abdomen 21 via an incision 80 in the abdominal wall. Laparoscope 82 allows the physician to view gallbladder 6 as the practitioner guides distendable bladder 5 through punctured tip 22 into the gallbladder. Prior to insertion of the distendable bladder 5 into the gallbladder 6, the physician has isolated the gallbladder from the common bile duct by placing clips 84 and 84' on cystic duct 86 with the aid of a clip applicator (not shown). Manipulation of the proximal end 7 of rigid tubing 3 may be assisted by grasping and holding the gallbladder 6 with known means, such as a first puncture clamp 4. A second puncture clamp which may be needed to stabilize the gallbladder during the procedure and an electrosurgical hook to isolate the cystic duct are not shown.

Figure 4:
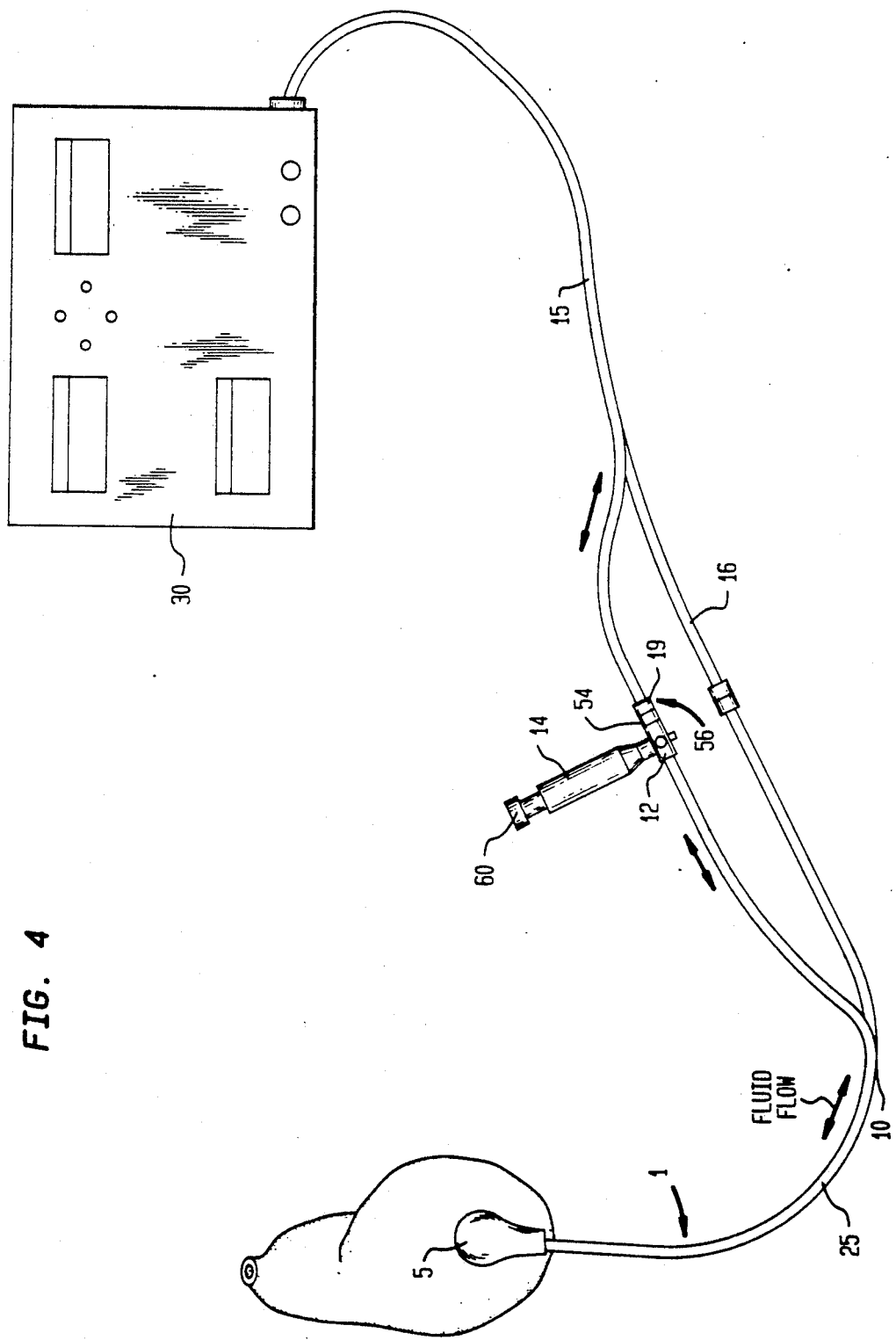
FIG. 4 is a view of an apparatus constructed in accordance with the invention which illustrates the catheter connections.

FIG. 4 illustrates the arrangement of control unit 30 and catheter end 1, comprising the distendable bladder 5, rigid tubing 3 and flexible tubing 10, and the interconnection of those elements. A fluid system 55 comprises that portion of the invention through which the fluid 25 travels, including a hypodermic barrel 14 or other fluid source (not shown), flexible tubing 10, rigid tubing 3, distendable bladder 5 and control unit 30. Manipulation of the hypodermic barrel 14 enables the operator of the system to control the amount of fluid 25 in the fluid system 55, inflation and deflation of the distendable bladder by adding or removing fluid, respectively, and pressure of the fluid 25 in the system. Hypodermic barrel 14 also provides protection for the patient by allowing fast and safe reduction of excessive pressures in the system.

Manipulation of the hypodermic barrel 14 by depressing a plunger 60 causes fluid 25 to be introduced through 3-way stopcock 12 into the flexible tubing 10, and to the rigid tubing 3. The fluid 25 emerges from rigid tubing 3 and into distendable bladder 5, forcing distendable bladder 5 to expand into contact with the inner tissue layer 27 of the gallbladder 6. The fluid 25 is also directed along the flexible tubing to the control unit 30 allowing measurement of the fluid pressure within the distendable bladder by well known means.

Each of the parts of the fluid system 55 is in fluid communication providing constant fluid pressure within the entire fluid system 55 and allowing measurement of the pressure at the catheter end 1 via measurement of pressure of the end attached to the control unit 30.

Control unit 30 is connected to catheter end 1 via plastic sheath 15 which contains flexible tubing 10 and electrical sheath 16. Flexible tubing 10 is connected to a fluid joint 56 via pressure transducer 54, by well known means. Using a standard luer lock connector 19, pressure transducer 54 and hypodermic barrel 14 are connected to flexible tubing 10 via a readily available 3-way stopcock 12. 3-way stopcock 12 may be used to isolate the hypodermic barrel 14 or other fluid source from the fluid system 55 once the desired fluid pressure is reached.

Figure 5:
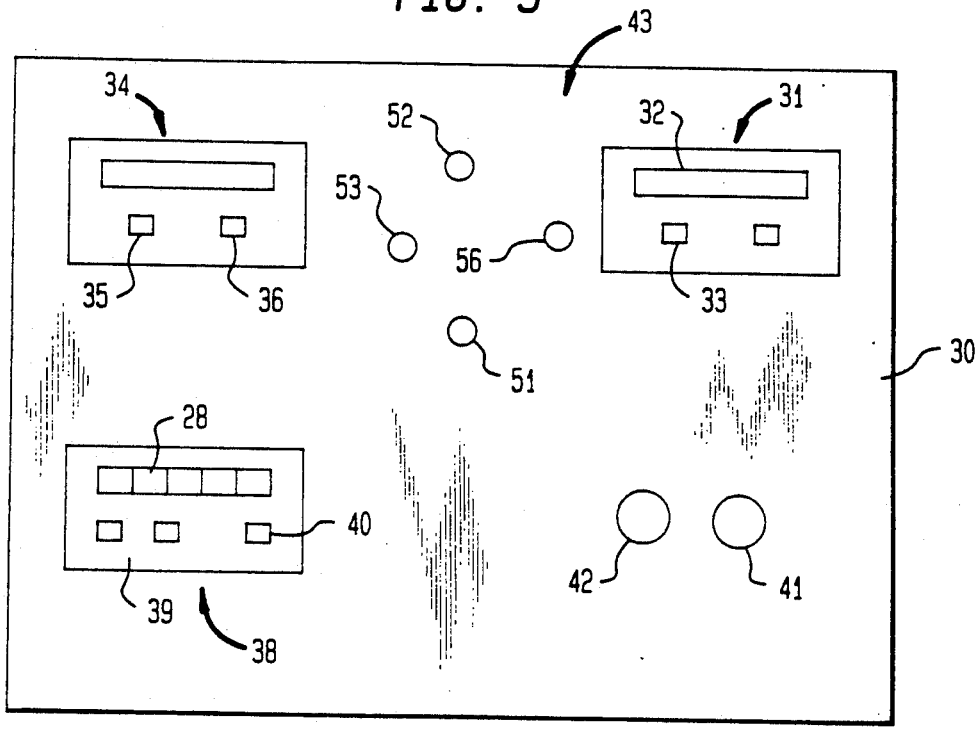
FIG. 5 illustrates a system control unit.

FIG. 5 illustrates control unit 30, consisting of fluid temperature control 31, fluid pressure control 34, time control 38' and a power source (not shown). The control unit 30 includes a power switch 42 and fuse 41. Fluid temperature is regulated by fluid temperature control 31 and is set by temperature set/reset button 33. The temperature of fluid 25 in the distendable bladder 5 is shown at temperature display 32.

Fluid pressure within the fluid system 55 may be monitored by means of controls located on fluid pressure control panel 34. The upper limit for fluid pressure is controlled by high pressure set/reset button 35, with the lower limit controlled by low pressure set/reset button 36. Fluid pressure in mmHg is shown by LED pressure display 37. Control unit 30 also has pressure indicator display 43, which upon introduction of fluid 25 into the fluid system 55 provides an easy to see visual display of fluid pressure within the fluid system 55.

Time for the procedure is shown at time display 38, which displays both lapsed time and time remaining for the procedure. Total time for the procedure may be easily set in minutes, seconds, and tenths of seconds using time set buttons 39 and may be cleared or reset using time clear/reset button 40.

Figure 6:
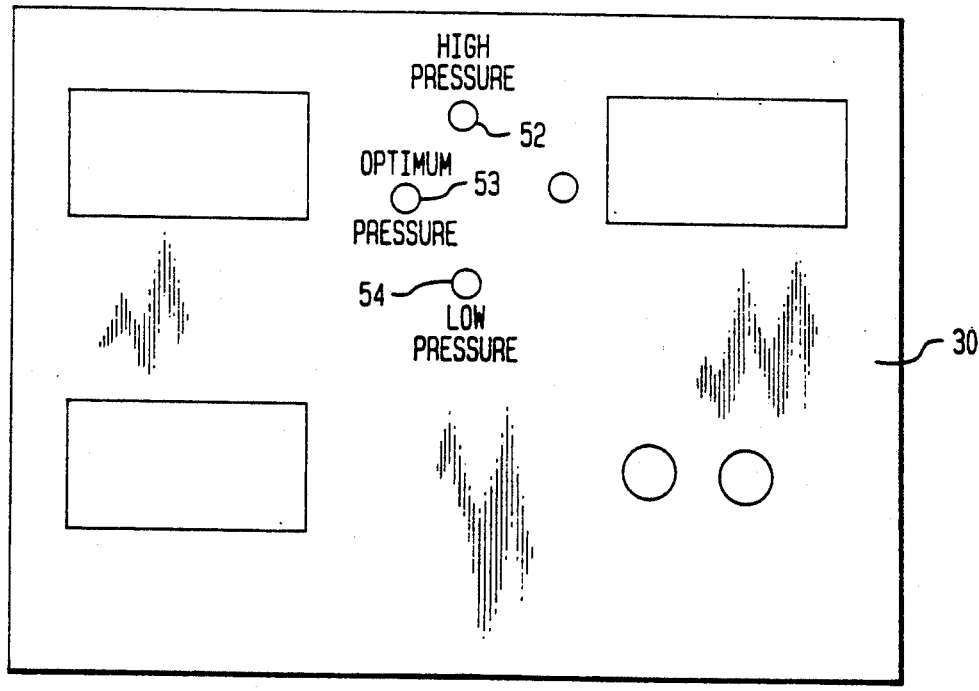
FIG. 6 is a detail view of a pressure limiting and safety monitor.

A simplified means for determining whether the fluid 25 is within the preset pressure range is depicted in FIG. 6, which illustrates the pressure indicator display 43. The pressure indicator display 43 is comprised of a low pressure indicator 51, a high pressure indicator 52 and an optimum pressure indicator 53. As fluid 25 is introduced into the fluid system 55 by manipulation of hypodermic barrel 13, the pressure indicator display 43 is successively illuminated as various fluid pressures are reached. Low pressure indicator 51 is illuminated when fluid pressure is below the preset range. High pressure indicator 52 is illuminated when fluid pressure is above the preset range. Optimum pressure indicator 53 is illuminated when fluid pressure is within the preset range.

These indicators allow the practitioner to readily reach the preset pressure range by varying the amount of fluid in the fluid system via manipulation of the hypodermic barrel 14. A separate heating element indicator 55 is also provided to indicate when power is being provided to a heating element 44 located within the distendable bladder 5.

Figure 7A:
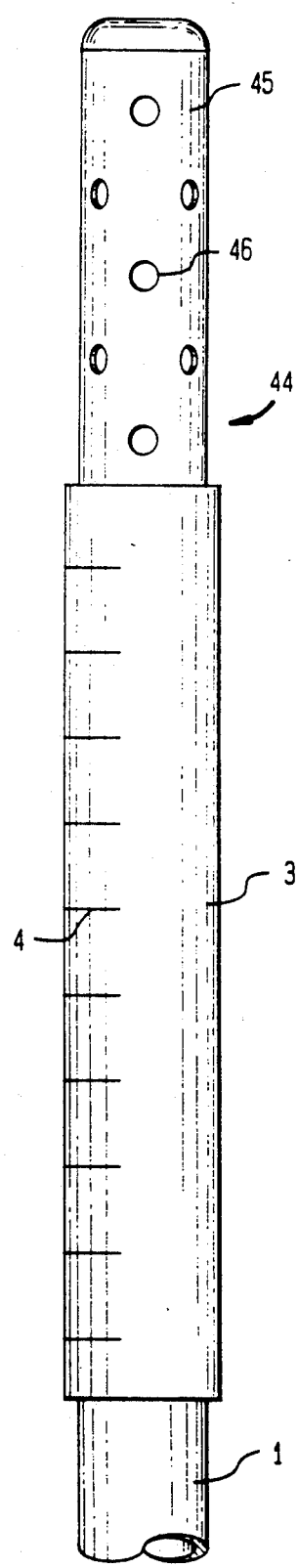
FIG. 7A is the vented heating element shield utilized in the method of the present invention.
Figure 7B:
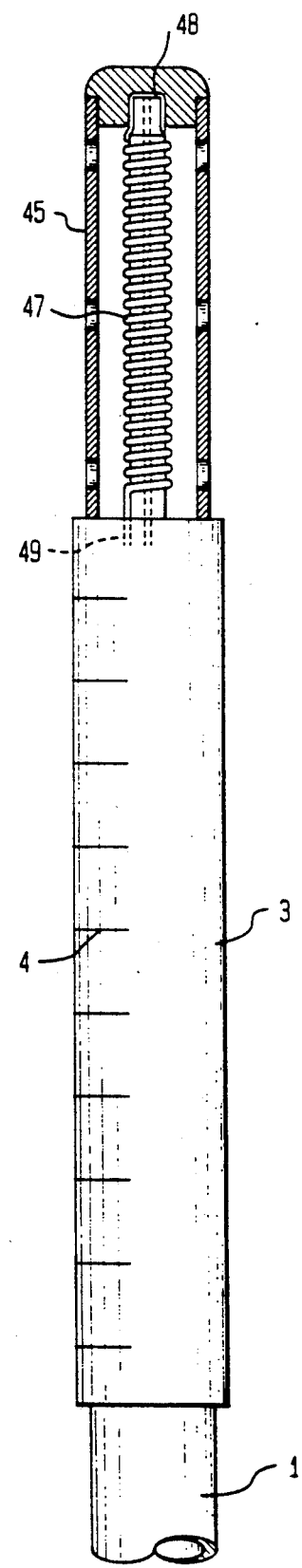
FIG. 7B is a cutaway view of the vented heating element shield showing the heating element and thermocouple.

Two views of heating element 44 are shown in FIGS. 7A and 7B. FIG. 7A is an external view of heating element 44, which comprises heating element coil shield 45 and ventilation holes 46.

FIG. 7B is a cutaway view of heating element 44, wherein wire leads 49 provide power from system control unit 30 to heating element coil 47 causing heating element coil 47 to heat the fluid 25 which comes into contact with the heating element coil 47 as the fluid 25 flows through the ventilation holes 46. Temperature of the fluid 25 is measured by thermocouple 48 and is displayed at temperature display 32. Heat element coil shield 45 prevents distendable bladder 5 from contacting the heating element coil 47.

Figure 8:
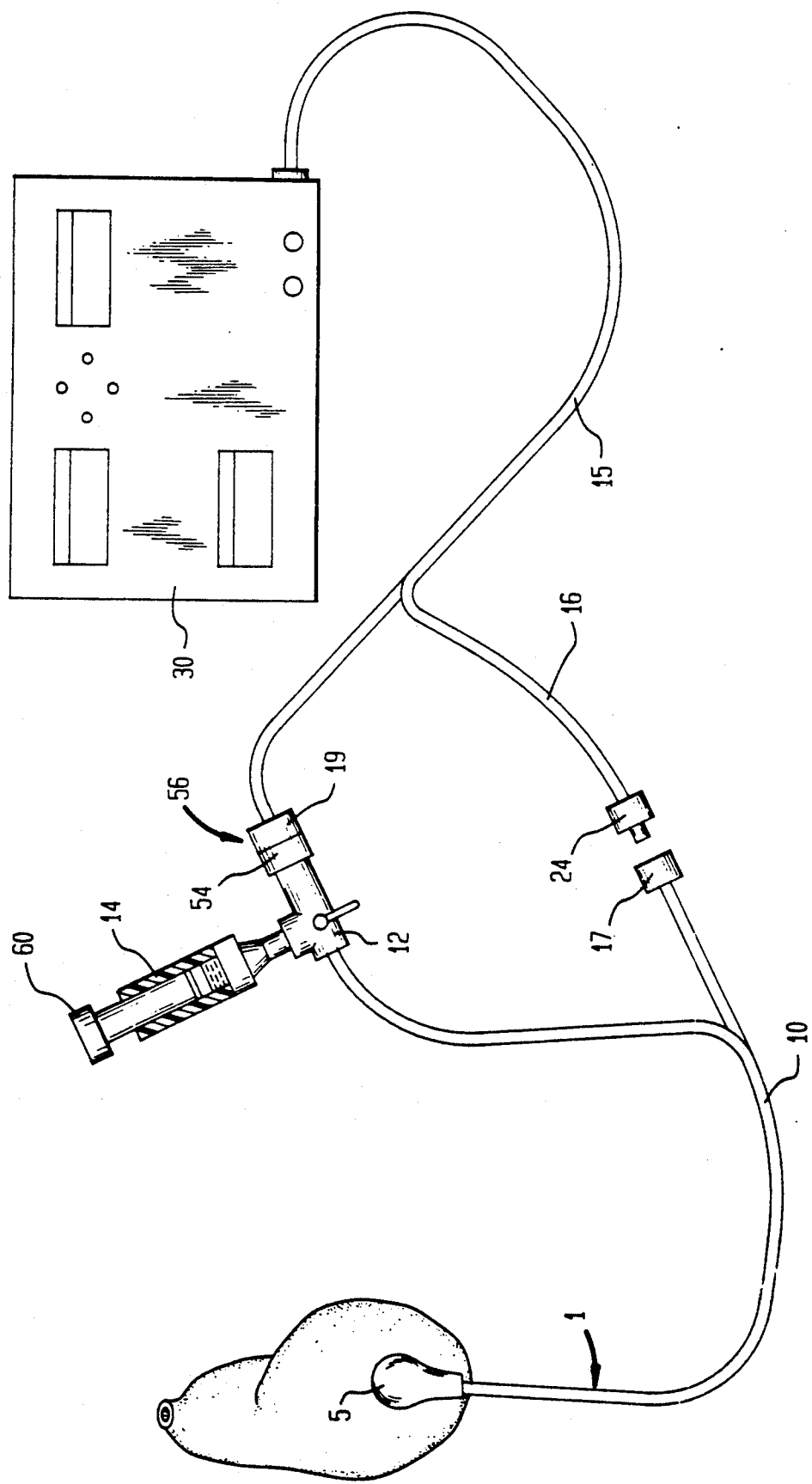
FIG. 8 illustrates a means for connecting and disconnecting the catheter.

The catheter end 1 is designed to be easy to replace as shown in FIG. 8, which illustrates control unit end 30' and catheter end 1 of the invention. Control unit end 30' is composed of electrical sheath 16 which is attached on one end to control unit 30 and on the other end to male electrical connector 24, which allows transmittal of power to the heating element 44. Male electrical connector 24 is readily attached or disattached to female electrical connector 17 on the catheter end 1.

Control unit end 30' is also comprised of components from the fluid system 55, including flexible tubing 10 attached to 3-way stopcock 12. 3-way stopcock 12 provides control over the introduction and removal of fluid 25 via hypodermic barrel 14. The catheter end 1 is easily connected or disconnected from the 3-way stopcock via a luer lock connector 19 attached to pressure transducer 54.

The invention will now be illustrated by the following examples.

EXAMPLE 1

The necrosis procedure is preceded by placing the patient in the supine position. An insufflation trocar is inserted through a periumbilical incision. Utilizing a WISAP® insufflator, the peritoneal cavity is insufflated with carbon dioxide to an intraperitoneal pressure of 20 mm of mercury (Hg) so as to separate the abdominal wall from the organs within the abdominal cavity. Next, a 10 mm laparoscope is inserted through the periumbilical trocar.

Following diagnostic laparoscopy, direct visualization is used to place two 4 mm trocars for the surgical procedure in the subcostal margin of the right upper quadrant. One 4 mm puncture wound is made to the right of the midline halfway between the xiphoid process and the umbilicus. A third 4 mm trocar is placed 2 inches to the right of the umbilicus.

Using a 5 mm probe, the liver is elevated for visualization and surgical access. Suction irrigation cannulae are placed through the punctures in the right upper quadrant. Subsequently an electrosurgical hook is used to expose the cystic duct. The inferior gallbladder is retracted with a first puncturing clamp and, using a clip applicator, the exposed cystic duct is doubly clipped with first and second clips. Grasping the gallbladder with a second puncture clamp so as to stabilize it, any stones in the gallbladder should be crushed with crushing down forceps. It is not necessary to sever the cystic artery.

The tip of the gallbladder is then punctured with a 4 mm trocar and cannula and remaining bile and crushed stones should be drained from the punctured gallbladder. The drained gallbladder is then gently irrigated with a sterile solution such as Ringer's Lactate® so as to clean the mucosa. The irrigation catheter may then be removed from the irrigation cannula, though it is also acceptable to remove the cannula after the catheter has been removed.

Under direct visualization, the distendable bladder is inserted into the puncture site or through the cannula if left in place. Once in place the catheter stem protrudes from the abdominal cavity and consists of an electrical connecting plug and rigid tubing. Placement of the catheter may be facilitated by distance markings on the rigid tubing indicating depth of insertion, although precise manipulation requires the laparoscope.

Upon placement of the distendable bladder, it will be connected to a control unit via attachment of the electrical connector and flexible tubing attached to the rigid tubing to their counterparts extending from the control unit.

Subsequent to insertion of the catheter, the control unit will be powered on in order to allow the practitioner to set the system constraints. The temperature of the fluid in the distendable bladder will be set at the temperature control panel and can be measured via the thermocouple located within the distendable bladder. Fluid pressure constraints are set at the pressure control panel, and upon inflation of the distendable bladder by introduction of fluid to the fluid system by depressing the plunger on the hypodermic barrel, can be easily measured by looking at the pressure indicator lights located on the control unit.

The practitioner then proceeds to inflate the distendable bladder by rotating the lever on the 3-way stopcock in order to access the fluid source and depressing the plunger on the hypodermic barrel which may serve as the fluid source. The practitioner injects the fluid into the fluid system until the pressure indicator lights indicate that the fluid pressure is within the pre-set constraints. At that point, the practitioner manipulates the 3-way stopcock to close off access to the fluid system by the fluid remaining in the hypodermic barrel. Thus, the fluid is non-circulating during the heating portion of the procedure, in part allowing more precise measurement of fluid temperature. The volume of fluid necessary to inflate the distendable bladder will vary from 10 to 50 ml in most cases in order to reach the pressure wherein the distendable bladder is substantially in contact with all of the inner tissue layer of the gallbladder.

The practitioner then turns on the heating element in order to heat the fluid to a pre-set level. The heating element in the distendable bladder is connected via the plug to a 12 volt system which will bring the fluid in the distendable bladder to the level of boiling as needed for each particular local, i.e. 190° Fahrenheit in Mexico City, and 212° Fahrenheit in New York City. Once that temperature level is reached, the system timer is activated to time the procedure and provide automatic turn off of the heating element at the end of a pre-set period. A heating phase of from about 2 to 6 minutes is preferred in order to completely necrose the mucosa. Monitoring of the procedure should continue with the laparoscope during the heating phase.

Upon completion of the procedure, the 3-way stopcock is again manipulated to allow the fluid to be withdrawn from the fluid system causing the distendable bladder to deflate. Upon deflation of the distendable bladder, the catheter may be safely withdrawn from the patient.

Following withdrawal of the deflated distendable bladder, a 4 mm bladder catheter drain is inserted into the open tip of the gallbladder and is then inflated prior to its being anchored within the gallbladder by known suturing means, such as by suturing it to an abdominal shunt.

Subsequently, the laparoscope and any remaining instruments are removed and the wounds are closed.

EXAMPLE 2

The present invention also provides a method for effecting removal of the urinary bladder neck blockage caused by a hypertrophied by heat destruction causing coagulative necrosis of the prostate to a depth of five to six millimeters. This procedure comprises insertion of a distendable bladder into the urinary bladder after cystoscopy, filling the urinary bladder with sorbitol, revealing the nature of the interior of the urinary bladder and the configuration of the enlarged prostate, inflating the distendable bladder with approximately 10 ml. of sterile 5% dextrose in water; retracting the distendable bladder against the urinary bladder neck and the hypertrophied prostate, heating the fluid in the distendable bladder to 195° Fahrenheit for about 5 minutes; deflating the bladder and withdrawing it from the bladder and urethra; then inserting an indwelling foley catheter for up to seven days to provide urine outflow during the period of swelling and edema following the heat injury. This post treatment period may be out of the hospital following which the bladder is removed and catheterization done only for urinary obstruction should debris from the necrotic prostate block urinary outflow. Success of the procedure can be determined by urinary symptoms as well as measuring the post voiding bladder residual volume of urine.

We claim:

1. A method for effecting necrosis of gallbladder tissue lining comprising the steps of:
   inserting a distendable bladder into the gallbladder;
   inflating the inserted bladder with an inflation medium to an appropriate volume to assure the bladder's contact with substantially all of the gallbladder tissue lining; and
   heating the inflating medium to about 190° fahrenheit for a period of about 2 to 6 minutes to effect necrosis of the tissue.

2. A method for effecting necrosis of gallbladder tissue lining comprising the steps of:
   making an incision into the abdominal cavity;
   inflating the abdomen with carbon dioxide so as to separate the abdominal wall from the organs within the abdomen;
   visualizing the gallbladder and liver with a laparoscope;
   grasping the gallbladder with a first puncture clamp;
   exposing the cystic duct with an electrosurgical hook;
   using a clip applicator to doubly clip the exposed cystic duct with first and second clips;
   grasping the gallbladder tip with a second puncture clamp so as to stabilize it;
   crushing stones in the stabilized gallbladder with crushing down forceps;
   puncturing the tip of the gallbladder with a 4 mm trocar and cannula;
   draining out the bile and crushed stones from the punctured gallbladder;
   irrigating the drained gall bladder with Ringer's Lactate so as to clean the mucosa;
   removing the irrigation catheter through the irrigation cannula;
   inserting a distendable bladder into the puncture site;
   inflating the inserted distendable bladder with an inflation medium to an appropriate volume in order to assure the bladder's contact with substantially all of the gallbladder's tissue lining;
   heating the inflation medium to about 190° fahrenheit for a period of about 2 to 6 minutes so as to cauterize the tissue lining;
   monitoring the heating phase with the laparoscope;
   deflating the bladder at the end of the heating phase;
   withdrawing the deflated bladder from the gallbladder;
   inserting a 4 mm bladder catheter drain into the tip of the gallbladder left open when the bladder was removed;
   inflating the inserted bladder catheter drain in order to anchor it within the gallbladder;
   suturing the inflated bladder catheter drain to the abdominal wall; removing the laparoscope, first clip, and closing the puncture wounds of the abdominal wall.

3. An apparatus for effecting necrosis of gallbladder tissue lining comprising:
   a catheter a proximal end and a distal end;
   distendable bladder means attached to said proximal end adapted for insertion into and distending the gallbladder;
   inflating means connected to said distal end for introducing an inflation medium into said distendable bladder;
   heating means for heating said inflation medium to a temperature sufficient to effect tissue necrosis positioned internal to said distendable bladder; and
   control means connected to said distal end for regulating the inflating and heating of said distendable bladder.

4. A method for effecting removal of bladder neck blockage caused by a hypertrophied prostate comprising the steps of:
   inserting a distendable bladder into the prostate;
   inflating the inserted bladder with an inflation medium to an appropriate volume to assure the bladder's contact with substantially all of the prostate's tissue lining; and
   heating the inflating medium to about 190° fahrenheit for a period of about 2 to 6 minutes to effect necrosis of the tissue.

5. A method for effecting removal of bladder neck blockage caused by a hypertrophied prostate comprising the steps of:
   inserting a distendable bladder into the bladder after cystoscopy;
   filling the urinary bladder with sorbitol;
   revealing the nature of the interior of the urinary bladder and the configuration of the hypertrophied prostate;
   inflating the inserted bladder with about 10 ml of sterile 5% dextrose in water;
   retracting the inflated bladder against the bladder neck and the hypertrophied prostate;
   heating the dextrose in water solution in the bladder to about 190° fahrenheit for about 5 minutes;
   deflating the bladder and withdrawing it from the bladder and urethra;
   inserting an indwelling foley catheter for about seven days to provide urine outflow during the period of swelling and edema following the procedure.

6. An apparatus for effecting removal of bladder neck blockage caused by a hypertrophied prostate comprising:
   a catheter a proximal end and a distal end;
   distendable bladder means attached to said proximal end adapted for insertion into and distending the prostate;
   inflating means connected to said distal end for introducing an inflation medium into said distendable bladder;
   heating means for heating said inflation medium to a temperature sufficient to effect tissue necrosis positioned internal to said distendable bladder; and
   control means connected to said distal end for regulating the inflating and heating of said distendable bladder.

* * * * *